(12) United States Patent
Culver et al.

(10) Patent No.: US 7,983,740 B2
(45) Date of Patent: Jul. 19, 2011

(54) HIGH PERFORMANCE IMAGING SYSTEM FOR DIFFUSE OPTICAL TOMOGRAPHY AND ASSOCIATED METHOD OF USE

(75) Inventors: Joseph Culver, Webster Groves, MO (US); Gavin Perry, Webster Groves, MO (US); Benjamin Zeff, University City, MO (US)

(73) Assignee: Washington University, St. Louis, MO (US)

( * ) Notice: Subject to any disclaimer, the term of this patent is extended or adjusted under 35 U.S.C. 154(b) by 590 days.

(21) Appl. No.: 11/962,513

(22) Filed: Dec. 21, 2007

(65) Prior Publication Data

US 2008/0154126 A1    Jun. 26, 2008

Related U.S. Application Data

(60) Provisional application No. 60/871,503, filed on Dec. 22, 2006.

(51) Int. Cl.
*A61B 6/00* (2006.01)
(52) U.S. Cl. .......................... 600/476; 600/473
(58) Field of Classification Search .................. 600/407, 600/473–476; 356/432–433, 435; 359/238, 359/278; 382/128, 131
See application file for complete search history.

(56) References Cited

U.S. PATENT DOCUMENTS

| | | | |
|---|---|---|---|
| 3,668,634 A | | 6/1972 | Kruklitis |
| 6,516,214 B1 | | 2/2003 | Boas |
| 6,526,309 B1 | * | 2/2003 | Chance ........................ 600/473 |
| 6,549,284 B1 | * | 4/2003 | Boas et al. ................... 356/446 |
| 6,615,063 B1 | * | 9/2003 | Ntziachristos et al. ....... 600/312 |
| 6,618,614 B1 | * | 9/2003 | Chance ........................ 600/473 |
| 7,010,341 B2 | * | 3/2006 | Chance ........................ 600/476 |
| 7,218,959 B2 | * | 5/2007 | Alfano et al. ................. 600/476 |
| 7,463,362 B2 | * | 12/2008 | Lasker et al. ................. 356/497 |
| 7,610,082 B2 | * | 10/2009 | Chance ........................ 600/475 |
| 7,617,080 B2 | * | 11/2009 | Barbour et al. ................... 703/2 |

(Continued)

FOREIGN PATENT DOCUMENTS

EP    1329700 A    7/2003

OTHER PUBLICATIONS

McKeown, Martin J. et al., Independent component analysis of functional MRI: what is signal and what is noise?, Current Opinion in Neurobiology, vol. 13, Oct. 2003, pp. 620-629.

(Continued)

*Primary Examiner* — Frances Jaworski
(74) *Attorney, Agent, or Firm* — Senniger Powers LLP

(57) ABSTRACT

A high performance imaging system for diffuse optical tomography is disclosed. A dense grid utilizing sources, e.g., light emitting diodes ("LEDs"), that achieve high performance at high speed with a high dynamic range and low inter-channel crosstalk are complemented by a system of discrete, isolated receivers, e.g., avalanche photodiodes ("APDs"). The source channels have dedicated reconfigurable encoding control signals, and the detector channels have reconfigurable decoding, allowing maximum flexibility and optimal mixtures of frequency and time encoding and decoding. Each detector channel is analyzed by dedicated, isolated, high-bandwidth receiver circuitry so that no channel gain switching is necessary. The resulting improvements to DOT system performance, e.g., increased dynamic range and decreased crosstalk, enable higher density imaging arrays and provide significantly enhanced DOT image quality. A processor can be utilized to provide sophisticated three dimensional modeling as well as noise reduction.

24 Claims, 18 Drawing Sheets

U.S. PATENT DOCUMENTS 7,720,525 B2 * 5/2010 Hall ............................ 600/473

OTHER PUBLICATIONS

Culver, J. et al., "Diffuse Optical Tomography for Mapping Human Brain Function," Life Science Systems and Applications Workshop, (Jul. 1, 2006), pp. 8.

Culver, J. et al., "Volumetric Diffuse Optical Tomography of Brain Activity," Nov. 1, 2003, vol. 28, No. 21, pp. 2061-2063, Optics Letters.

Culver, J. et al., "Diffuse Optical Tomography of Cerebral Blood Flow, Oxygenation, and Metabolism in Rat During Focal Ischemia", Journal of Cerebral Blood Flow & Metabolism, Apr. 17, 2003, vol. 23, pp. 911-924, The International Society for Cerebral Blood Flow and Metabolism, Published by Lippincott Williams & Wilkins, Inc., Baltimore.

Dehghani H. et al., "Multiwavelength Three-Dimensional Near-Infrared Tomography of the Breast: Initial Simulation, Phantom, and Clinical Results", Applied Optics 2003; vol. 42, pp. 135-145.

Fox, Michael D. et al., "The Human Brain is Intrinsically Organized into Dynamic, Anticorrelated Functional Networks", Proceedings of the National Academy of Sciences of the United States of America 2005; vol. 102, pp. 9673-9678.

Saager, Rolf B. and Berger, A., "Direct Characterization and Removal of Interfering Absorption Trends in Two-Layer Turbid Media", Journal of the Optical Society of America a-Optics Image Science and Vision 2005; vol. 22, pp. 1874-1882.

Hyvarinen A. Fast and Robust Fixed-Point Algorithms for Independent Component Analysis, IEEE Transactions on Neural Networks, 1999; vol. 10, pp. 626-634.

Hyvarinen A. and Oja, E., "Independent Component Analysis: Algorithms and Applications", Neural Networks 2000; vol. 13, pp. 411-430.

Onton J. et al., "Imaging Human EEG Dynamics Using Independent Component Analysis", Neuroscience and Biobehavioral Reviews 2006; vol. 30, pp. 808-822.

Mantini D. et al., "Complete Artifact Removal for EEG Recorded During Continuous Fmri Using Independent Component Analysis", Neuroimage 2007; vol. 34, pp. 598-607.

* cited by examiner

HIGH PERFORMANCE IMAGING SYSTEM FOR DIFFUSE OPTICAL TOMOGRAPHY AND ASSOCIATED METHOD OF USE

CROSS REFERENCE TO RELATED APPLICATIONS

This application claims the benefit of U.S. Provisional Application No. 60/871,503 filed Dec. 22, 2006, which is hereby incorporated by reference in its entirety.

STATEMENT REGARDING FEDERALLY SPONSORED RESEARCH & DEVELOPMENT

This invention was made with government support under grants NIH:NINDS K25 NS44339 A Jul. 1, 2002-Jun. 30, 2007 awarded by the U.S, National Institutes of Health. The government has certain rights in the invention.

BACKGROUND OF THE INVENTION

Diffuse optical imaging ("DOI") is an imaging methodology that can be utilized in mapping the functional activity in the human brain. With unique capabilities that include functional neuroimaging method, DOI complements and expands upon the other more established modalities such as Positron Emission Tomography ("PET") and Magnetic Resonance Imaging ("MRI"). While tremendously useful, the scanning environments of MRI and PET brain instruments generally require a fixed head placement in an enclosed tube, with significant scanner noise such as that found with MRI or the use of radioactive isotopes such as that found with PET.

In marked contrast to the more expensive scanner based technology (e.g. MRI and PET), DOI employs a less extensive technology platform and a wearable imaging cap. The DOI cap is well suited for several situations that are not amenable to fixed scanner environments, including the ability to obtain images of moving subjects who might otherwise require sedation, unmovable subjects, non-communicative subjects, patients in intensive care, subjects with metal implants, as well as studies of human development in children that would benefit from enriched ecological environments for a wider range of behavioral paradigms. The application that has particularly high potential is the use of DOI for critical care monitoring of infants and neonates.

Diffuse Optical Imaging ("DOI") builds images out of a number of discrete source and detector pair ("optode-pair") near-infrared spectroscopic samplings that are made non-invasively. When there is a single point measurement that is utilized without imaging, utilizing one or just a few optode pairs, the technique is referred to as near-infrared spectroscopy ("NIRS").

Previous diffuse optical neuroimaging systems have utilized sparse imaging arrays such as that disclosed in FIG. 1, which are generally indicated by numeral 10. In this scenario, sources are indicated by numeral 12 and detectors are indicated by numeral 14. The lines shown between the sources and detectors are the available source-detector measurement pairs, which are configured only as nearest neighbor optode pairs.

Referring now to FIG. 2, illustrating a sparse optode grid is generally indicated by numeral 20 in which the sources are indicated by numeral 24 and the receptors are indicated by numeral 26. The recreated simulated image is generally indicated by numeral 30 where the simulated reconstructed image for analysis is indicated by numeral 32.

The most extensively utilized NIRS brain imaging machine is restricted to first ($1^{st}$) nearest neighbor measurements only and topography, e.g., HITACHI® ETG-100 OT and ETG-400 OT, although high frame rates can be achieved. The type of system and the use of the nearest neighbor optode pairs have limited lateral resolution and no depth-sectioning capabilities. Simulations indicate that increasing the density of the optode arrays can improve resolution, localization and cerebral signal discrimination. However high density optode grids place stringent requirements upon the dynamic range, crosstalk, channel count and bandwidth performance specifications of the instrumentation, and these challenges are unmet by previous systems.

FIG. 3 illustrates a rudimentary flowchart of a prior art source detector multiplexing system, which is generally indicated by numeral 100. Typically an analog input and output device indicated by 110 is connected to analog sources 112 which are then multiplexed 114, typically time encoding of the signal, into different source optode locations provided through a plurality of connectors 115 to the measurement subject, e.g., human user, 116. After interacting with the measurement subject, e.g., human user, 116, the detector multiplexing system 118 decodes the time coding via light conductors 117, e.g., fiber optic cables. The light is then received by the detectors 120 and preprocessed in the gain stages 122 and then stored. The signal is converted to a digital signal through the analog digital converter 124. All of the illustrated stages 110, 112, 114, 118, 120, 122 and 124 take into account any change in encoding strategy or optode grid design.

A typical detector system is indicated by numeral 130 in FIG. 4. Light 131 is received in a series of channels 132 through a plurality of detectors 133, e.g., silicon photo diodes ("SiPD") that are connected to a programmable gain stage 134. After the first gain stage 134, there are a plurality of lock-in stages generally indicated by numeral 140. A lock-in frequency is a type of amplifier that can extract a signal with a known carrier wave from a noisy environment. There are represented a first lock-in frequency amplifier 142 and a second lock-in-frequency amplifier 144 for extracting at least two separate frequencies. The signals, after passing through programmable gain arrays 145, are then sent to sampling and hold stages 146. These digital signals are then provided to a processor 148. Therefore, there are significant issues when it comes to multiplexing as well as other significant issues involving both dynamic range and crosstalk. The present invention is directed to overcoming one or more of the problems set forth above.

SUMMARY OF INVENTION

The present invention achieves high performance at high speed with a high dynamic range, low crosstalk with a system of discrete isolated sources. The source has a dedicated high-bandwidth of at least one megahertz, e.g., twenty megahertz, (digital input/output line that can be individually programmed). The source multiplexing takes place entirely within the digital domain. Each light source, e.g., light emitting diode, has individual, isolated power to reduce crosstalk. Light emitting diodes as well as laser diodes have a threshold voltage below which they do not produce any light. When utilized in conjunction with individual digital control lines, the threshold voltage will squelch crosstalk. The small signal will not produce a light emitting diode output. Therefore, as a result of the above listed features, there is no measurable optical (light) crosstalk or cross source channels. Also, although the source control is digital, the high bandwidth at the control lines allows for variable intensity control of the sources through a high rate, variable duty pulsing. Also, the present invention allows for use of multi-furcated, e.g., bifurcated, optical fibers with two (2) or more colors of light multiplexed through a single source location.

The present invention achieves high performance at high speed with a high dynamic range and low crosstalk with a system of discrete, isolated avalanche photo diodes ("APDs"). Each detector channel has a dedicated APD so no gain switching is necessary. There are preferably isolated power sources for each isolated avalanche photo diode (APD) for signal isolation and to reduce crosstalk. Utilizing high-end commercial analog-to-digital converters, e.g., 24 bit analog-to-digital converters, digitize the signal output. A channel dedicated line eliminates gain switching. The units have very little noise and inter-channel crosstalk and all the data can be stored directly to a hard disk in real time with a sampling rate, e.g., 96 KHz. The separation of signals, otherwise known as decoding frequency encoding, is preferably carried out with software which allows maximum flexibility to determine the number of encoding frequencies.

These are merely some of the innumerable aspects of the present invention and should not be deemed an all-inclusive listing of the innumerable aspects associated with the present invention.

BRIEF DESCRIPTION OF THE DRAWINGS

For a better understanding of the present invention, reference may be made to accompanying drawings, in which.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well known methods, procedures, and components have not been described in detail so as not to obscure the present invention.

Figure 5:
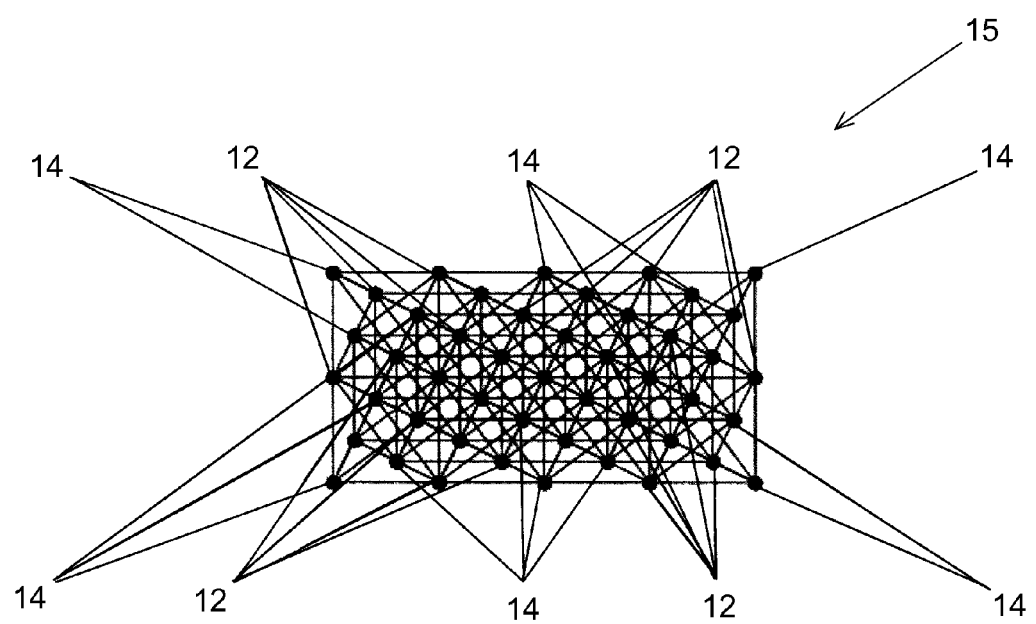
FIG. 5 is a representation of diffuse optical imaging utilizing high density optode pairs.

An improvement over diffuse optical imaging is a dense grid imaging array as shown in FIG. 5 and is generally indicated by numeral 15. In this situation, measurements are taken over multiple source detector distances with the sources identified by numeral 12 and detectors indicated by numeral 14. This high density array significantly improves lateral resolution and allows for volumetric localization of the functional signals. This is also known as depth profiling. These high density diffuse optical arrays involve many more source detector measurements with overlapping samplings that also permit diffuse optical tomography (DOT) reconstructions. However, high density diffuse optical tomography is very challenging due to the very high dynamic range and low crosstalk needed to simultaneously measure multiple signals at multiple distances with a significant number of measurements. Dynamic range is defined as the ratio of the maximum light power divided by the minimum detectable light power (or noise equivalent light level power). Furthermore, neuroimaging involves imaging a variety of time variant physiology, including heart pulse (one (1) Hertz), breathing (0.1 to 1 Hertz), and neuronally activated hemodynamic (0.001-0.3 Hertz) and fast scattering (ten (10) Hertz to One Thousand (1K) Hertz) responses. Therefore, high speed frame rates of greater than one (1) Hertz are critical and significant advantages are gained as frame rates progress in speed up to One Thousand (1K) Hertz. The dynamic range and crosstalk requirements must be maintained at the operating frame rate.

Low speed and significant crosstalk can render high density diffuse optical tomography useless. "Crosstalk" is defined as the leakage (or "bleeding") of signal from one channel into another. In this system we have source channels, detector channels and source-detector pair channels. The most stringent test of crosstalk is between source-detector pair channels. Crosstalk between source channels or between detector channels creates crosstalk between source-detector channels.

Figure 1:
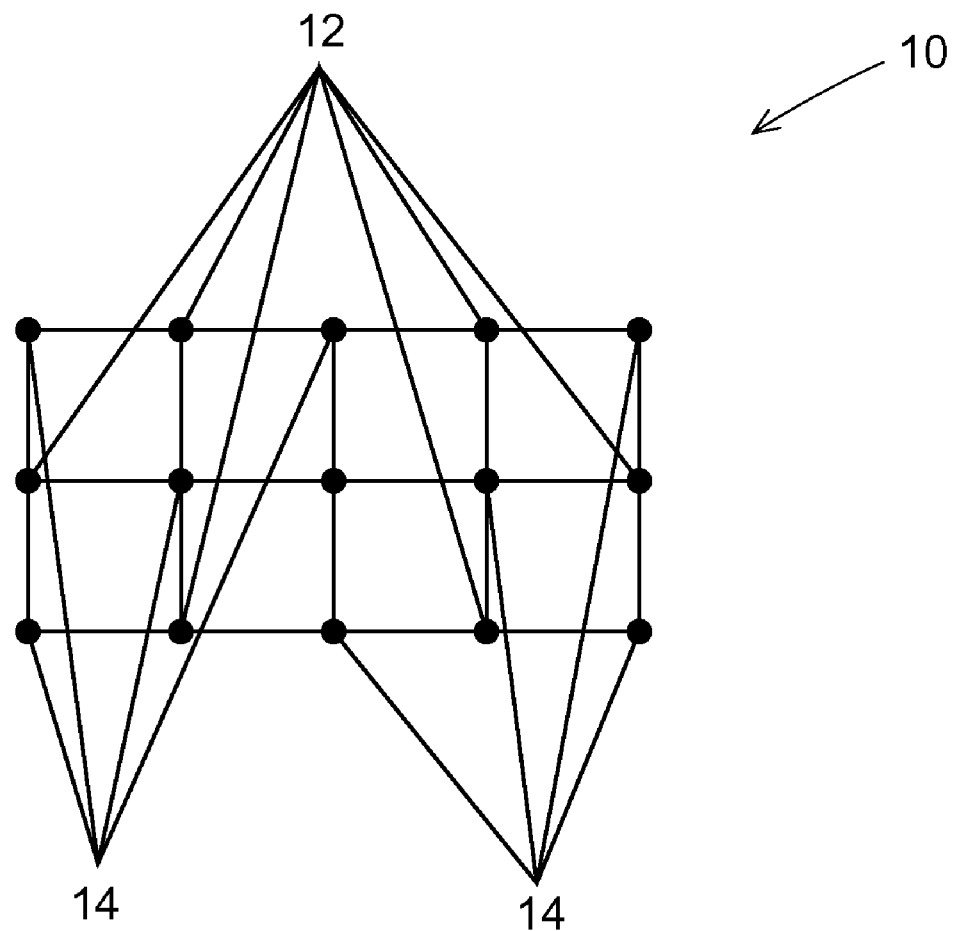
FIG. 1 is a representation of diffuse optical imaging utilizing sparse optode pairs.
Figure 2:
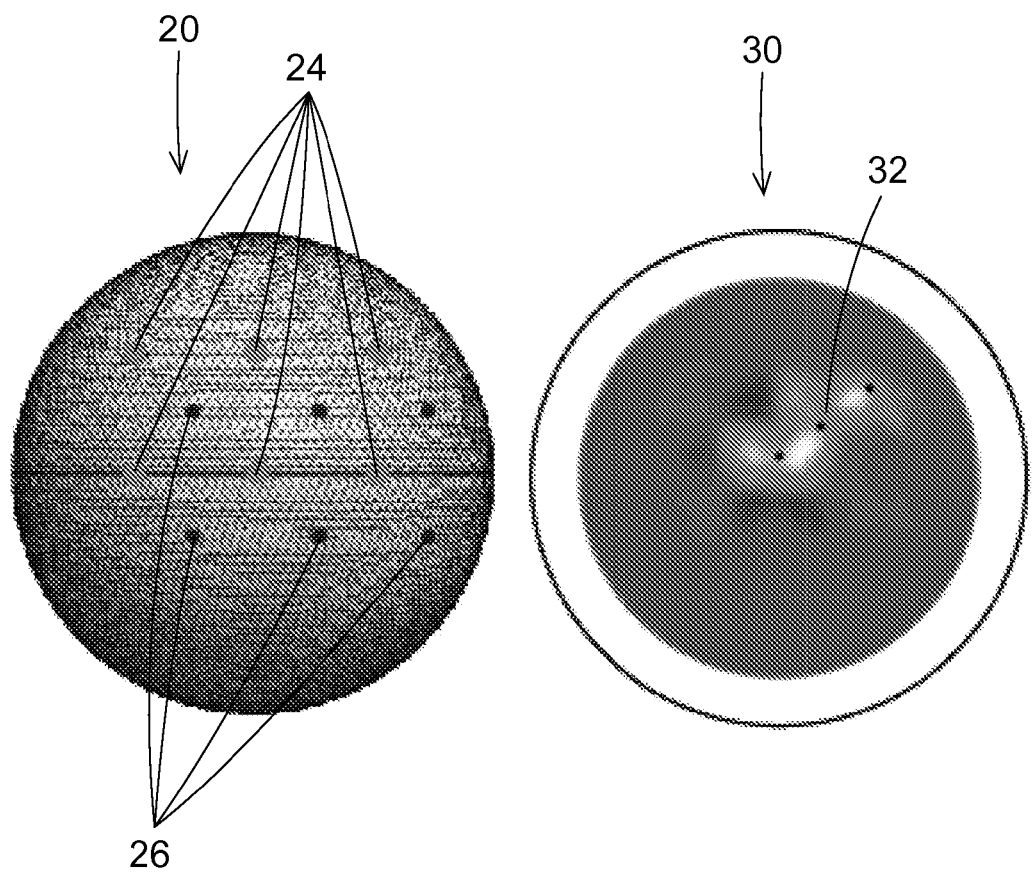
FIG. 2 is a representation of image quality, with image reconstruction, for diffuse optical imaging utilizing sparse optode pairs.
Figure 3:
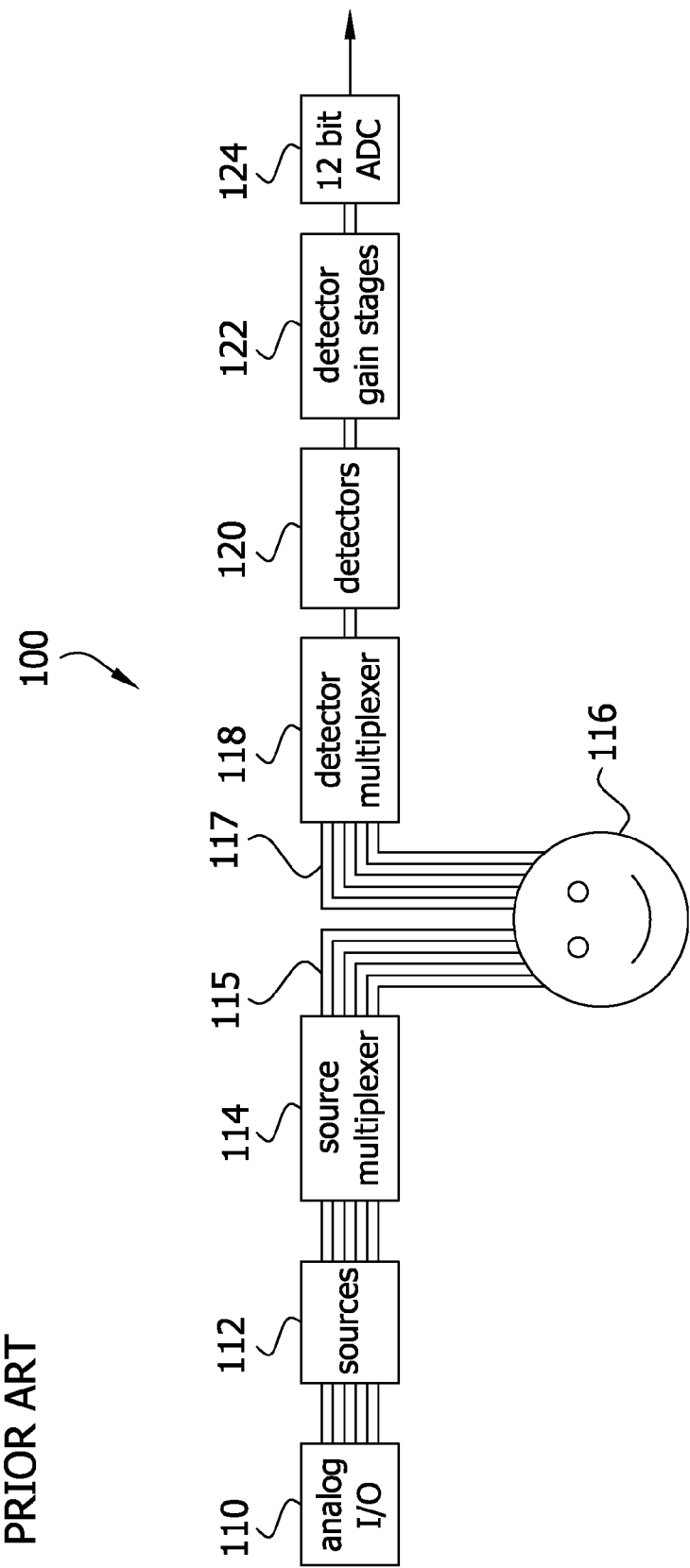
FIG. 3 is a flowchart of source and detector multiplexing and gain stages.
Figure 4:
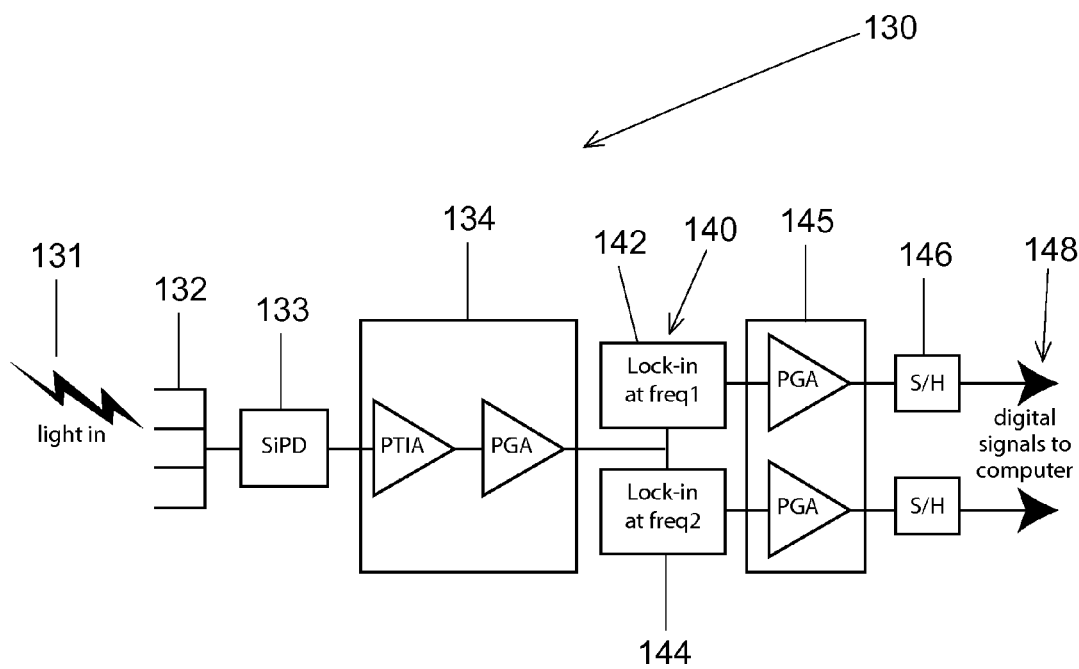
FIG. 4 is a flowchart of detection system with a series of programmable gain stages.

While a number of improvements have been recently proposed there are still significant unmet challenges involving both dynamic range and crosstalk. For example, as shown in FIG. 5, the high density optode grid indicated by numeral 15 presents significant challenges over the low density optode grid indicated by numeral 10 in FIG. 1. Therefore, in FIG. 1 with the sparse grid 10, the detectors need only the dynamic range to accommodate the range of intensities in the nearest neighbor signals, where dynamic range is the signal to dark noise level. In the high density grid 15 of FIG. 5, the dynamic range must be large enough to measure the high signals from the nearest neighbor pairs and the very small signal variations from the third ($3^{rd}$) nearest neighbor pairs. The problem of crosstalk occurs when the signal from one optode pair measurement registers on another measurement channel. With a broader range of signal levels being measured, sensitivity to crosstalk is enhanced in the dense grids 15 of FIG. 5. Crosstalk can occur at the source level when the output signal from one source is also included in the output provided by other sources. At the detector level, a signal from one detector may bleed over to other detector channels and a similar situation can occur in the analog-to-digital circuitry. The presence of crosstalk is a significant problem that corrupts the signal quality in important lower level channels and must be minimized to facilitate tomography.

Figure 6:
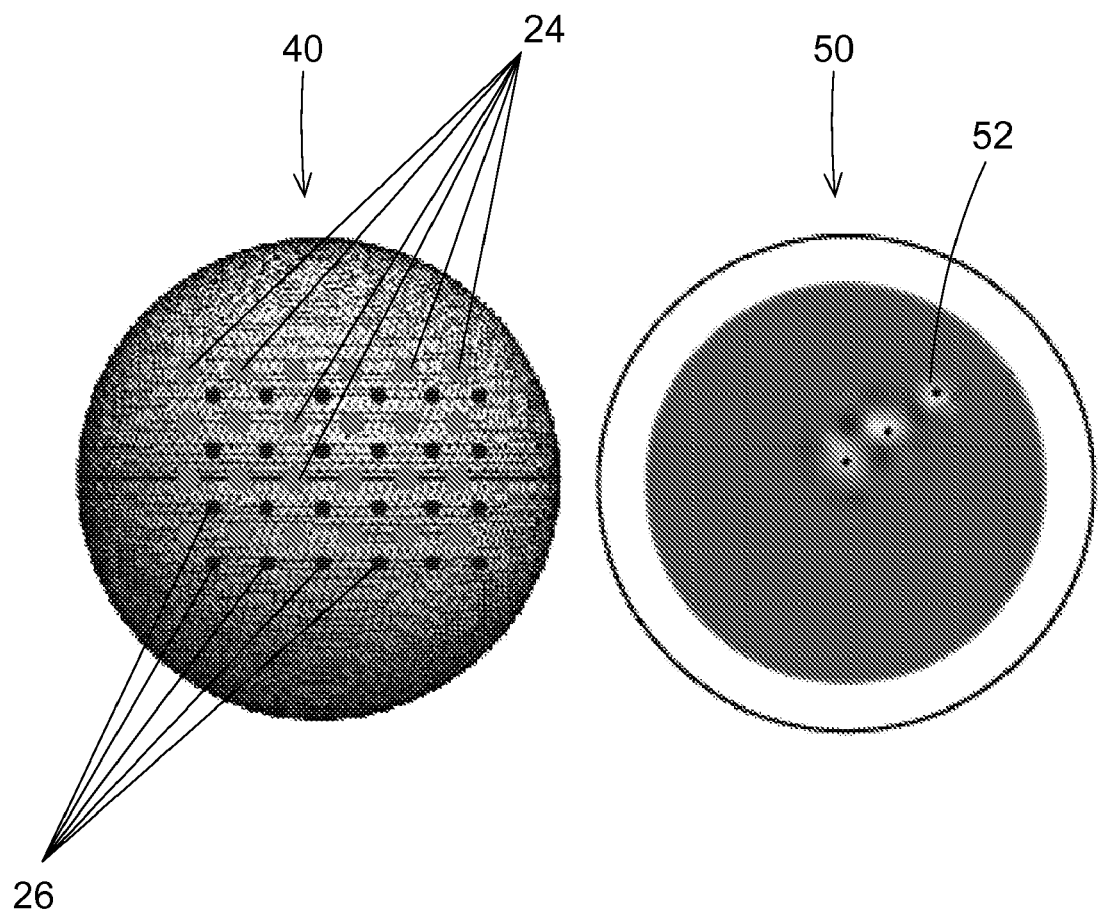
FIG. 6 is a representation of image quality, with image reconstruction, for diffuse optical imaging utilizing dense optode pairs.

FIG. 6 illustrates a preferred dense grids generally indicated by numeral 40, with the dense optode grid which includes sources indicated by numeral 24 and detectors indicated by numeral 26. The simulated image is generally indicated by numeral 50 with the stimulated image reconstruction indicated by numeral 52. There are a number of approaches to try to increase the speed of the system as well as decrease crosstalk. This typically involves some type of encoding strategy.

Different encoding strategies include time encoding, frequency encoding and spatial encoding. Time encoding decreases signal crosstalk by switching only particular sources at a particular time step. Frequency encoding involves assigning specific modulation frequencies to different signals, which allows multiple sources to be on simultaneously and increases the measurement rate of the system. Frequency specific detection schemes which separate out the required signals have their inter-channel separation limited by the level of background shot noise. Spatial encoding also increases the measurement rate by allowing optode pairs in different regions of the pad to be on simultaneously. Spatial separation provides another approach to reducing crosstalk, but is only useful for distant optodes and does not provide much assistance in reducing crosstalk for optodes that are close together. The combination of all three encoding strategies have significant drawbacks since a high level of system flexibility is required even though optimization of image quality for a variety of head sizes and imaging tasks is achieved.

The alternative means for depth sectioning includes the previously mentioned high density optode grid measurements. The greater source detector separations allow sampling deeper into the tissue; therefore, simultaneous measurements at multiple separation distances can provide the necessary information to separate depth dependent signals. There have been several proposed multi distance measurement systems that have been proposed for brain imaging. Examples include the DYNOT™ system by NIRX™ which has 32 sources and 32 detectors and the ISS Imagent system with eight (8) detectors and two (2) continuous wave ("CW") systems developed by Massachusetts General Hospital known as "CW4" which has nine (9) sources and sixteen (16) detectors and "CW5" which has 16 sources and 32 detectors.

A limitation common to these systems is the use of time-shared, multiplexed analog-to-digital converters (ADCs). Generally, multiplexed analog-to-digital converter acquisition cards have inter-channel crosstalk values of greater than −75 dB. In particularly, sixteen (16) bit analog-to-digital converters have been used which have an inherent dynamic range of less than $10^5$ in many systems, analog gain adjustments are made to match the signal range (dark noise to maximum signal) for a given measurement to the range of analog-to-digital converter electronics. These dynamic gain adjustments between neighboring channels can increase the effective crosstalk between detector channels and the effective dynamic range of the instrument. However, these dynamic gain adjustments at high speeds become very complex and are prone to new sources of channel crosstalk. The time shared adjustable detector circuitry limits the number of measurements that can be taken simultaneously and affects the overall speed of the system.

Another significant weakness of the previously described high channel count DOT systems is the use of source encoding and decoding strategies that are determined and implemented by hardware. Examples include fully timed multiplexed light sources in which a single light source is shared between multiple source locations or fully frequency encoded systems or a fixed mixture of frequency and time encoding. These hardware approaches dramatically decrease the flexibility with regard to encoding strategy resulting in increased crosstalk, decreased signal noise ratios, slower imaging times and degraded image quality.

Figure 7:
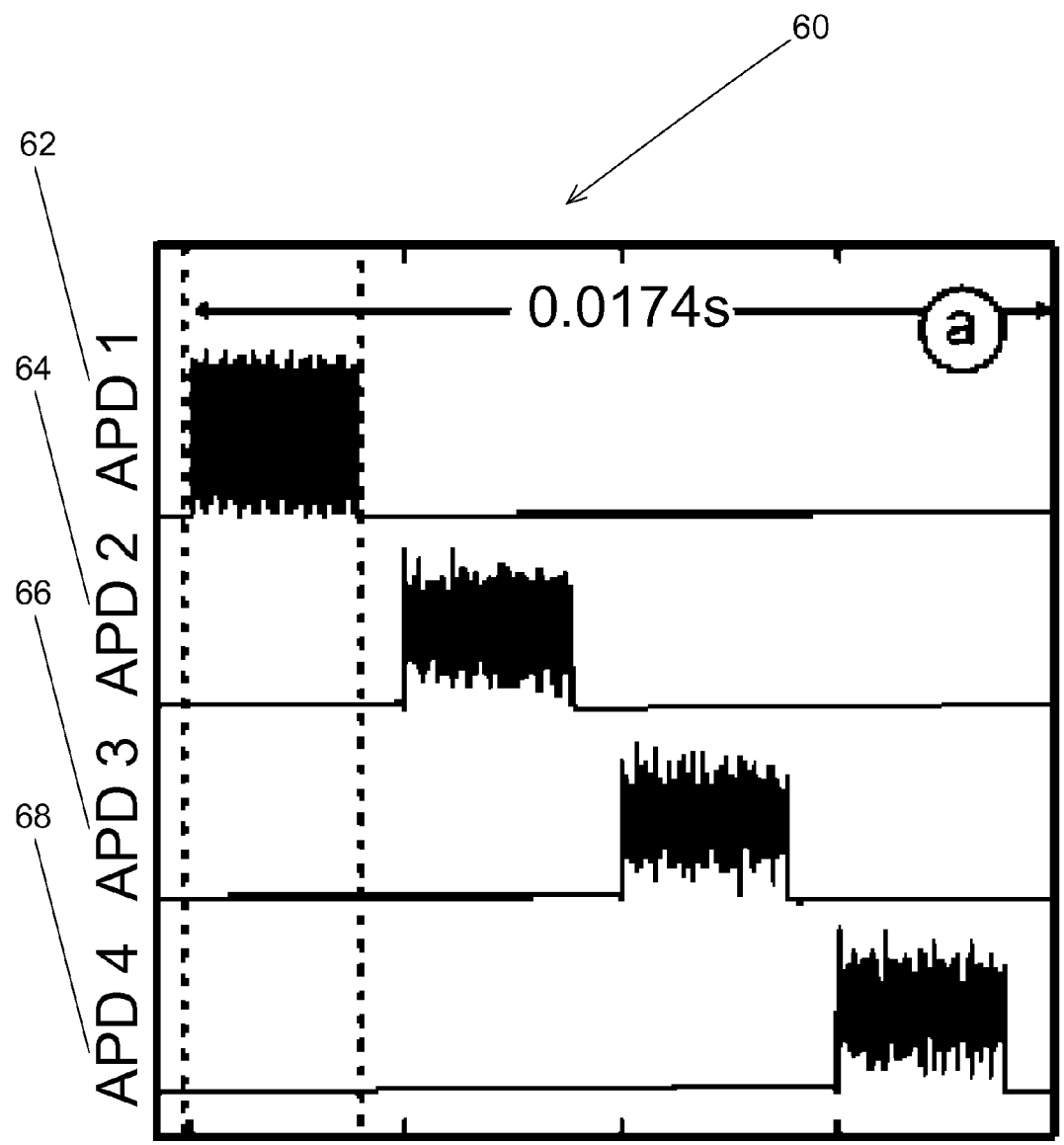
FIG. 7 is a graphical representation of time encoding of four sources coupled with four detectors.
Figure 8:
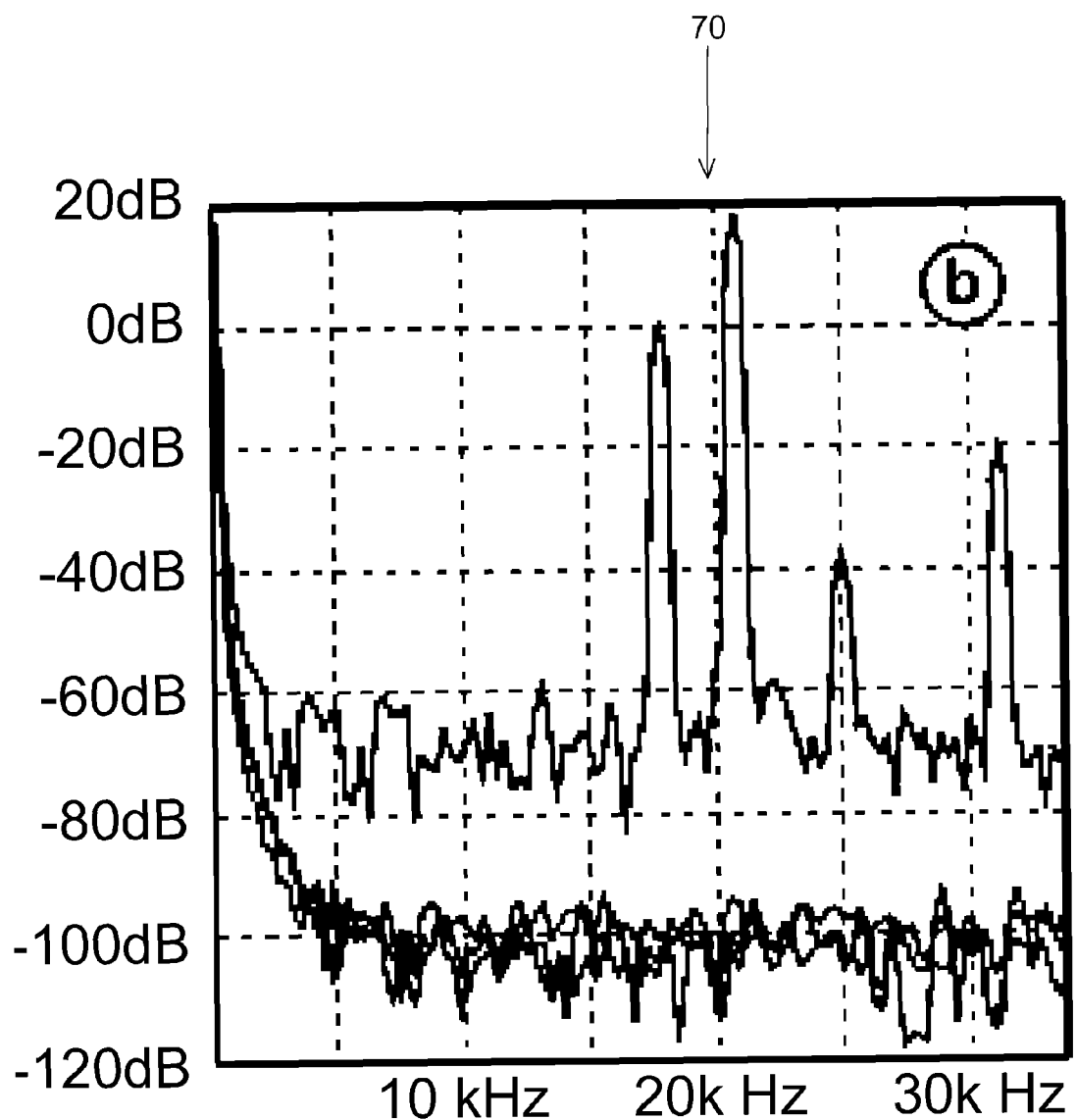
FIG. 8 is a graphical representation of frequency encoding of four sources coupled with four detectors with only one signal capable of being shown.
Figure 9:
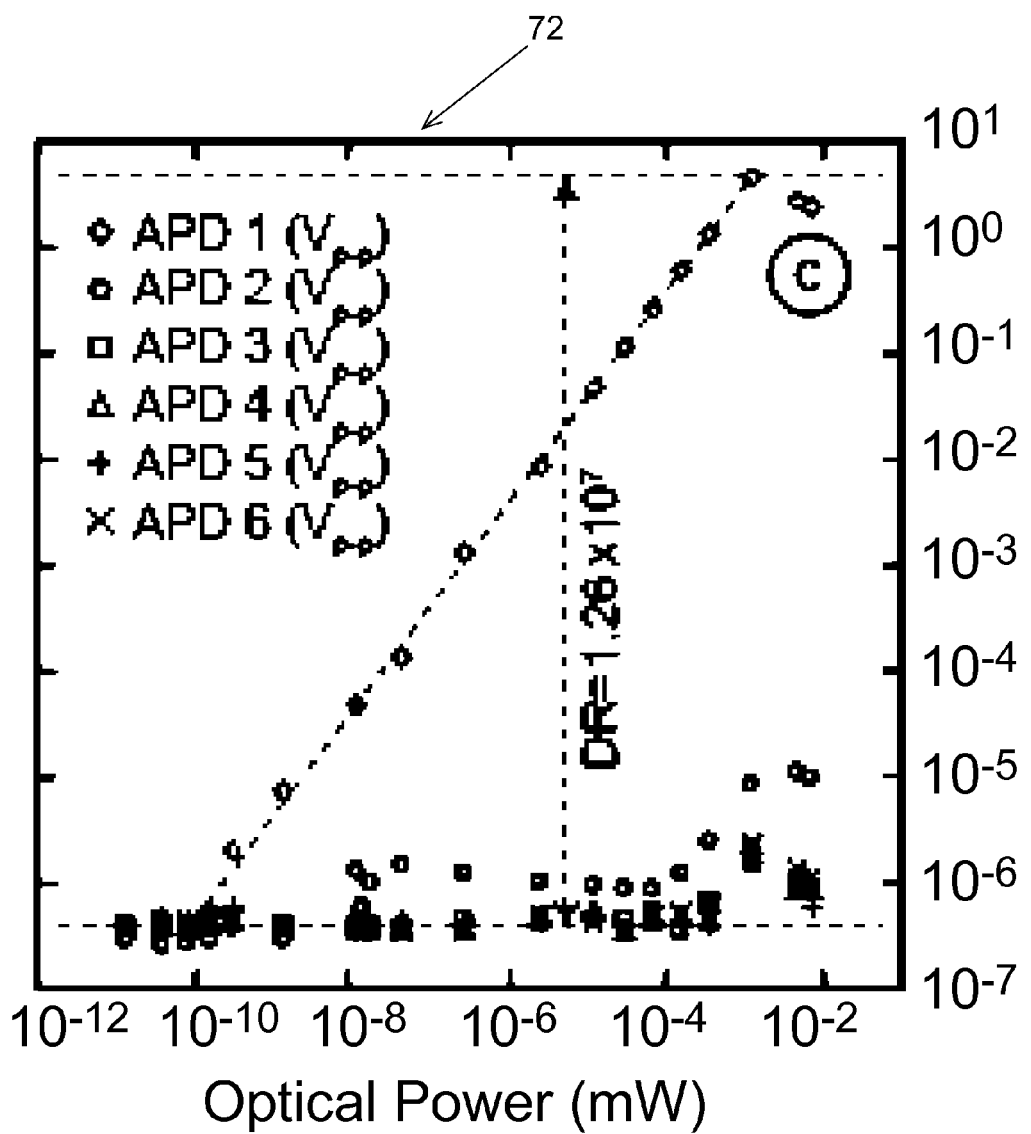
FIG. 9 is a graphical representation of a range of optical power that can be measured on a single channel with no gain switching.

Our system utilizes a flexible fully reconfigurable mixture of time and frequency encoding that is determined in software and/or firmware. An example of the various approaches possible with the new system include time encoding the signals with the four sources coupled with four different detectors, which is generally indicated by numeral 60 in FIG. 7. The sources are turned on in sequence with each signal visible on only a single detector for modulation frequencies present in each signal trace indicated by numerals 62, 64, 66 and 68. Referring now to FIG. 8, the frequency decoding of the first signal found in FIG. 7 with all four detectors is displayed. Modulation frequencies are picked up strongly on one detector but are not visible on the other three, which is generally indicated by numeral 70. The 120 dB range corresponds to a crosstalk rejection of less than $10^{-6}$. FIG. 9, which is generally indicated by numeral 72, displays a range of optical power that can be measured on a single detector channel with no gain switching and is typically greater than $10^7$ (bandwidth 1 Hz).

The present invention is a high density diffuse optical tomography system that is instantaneous with a high dynamic range. High performance is defined as including a high dynamic range of at least $10^5$, preferably at least $10^6$, and optimally at least $10^7$, crosstalk as being at least less than $10^{-5}$, preferably less than $3 \times 10^{-6}$ and optimally less than $10^{-6}$, and a frame rate as being greater than one (1) Hertz, preferably greater than three (3) Hertz, and optimally greater than ten (10) Hertz. The system utilizes isolated and discrete source detector channel circuitry and the signals only become multiplexed in the digital domain. The hardware for the present invention is indicated by numeral 200 in FIG. 10, with the electrical connectors going to the sources and from the receptors generally indicated by numeral 212. The hardware 200 preferably includes a processor, which can be a digital signal processor, a personal computer, or a controller, however, any of a wide variety of electronic computers or electronic controllers will suffice.

Figures 10, 11:
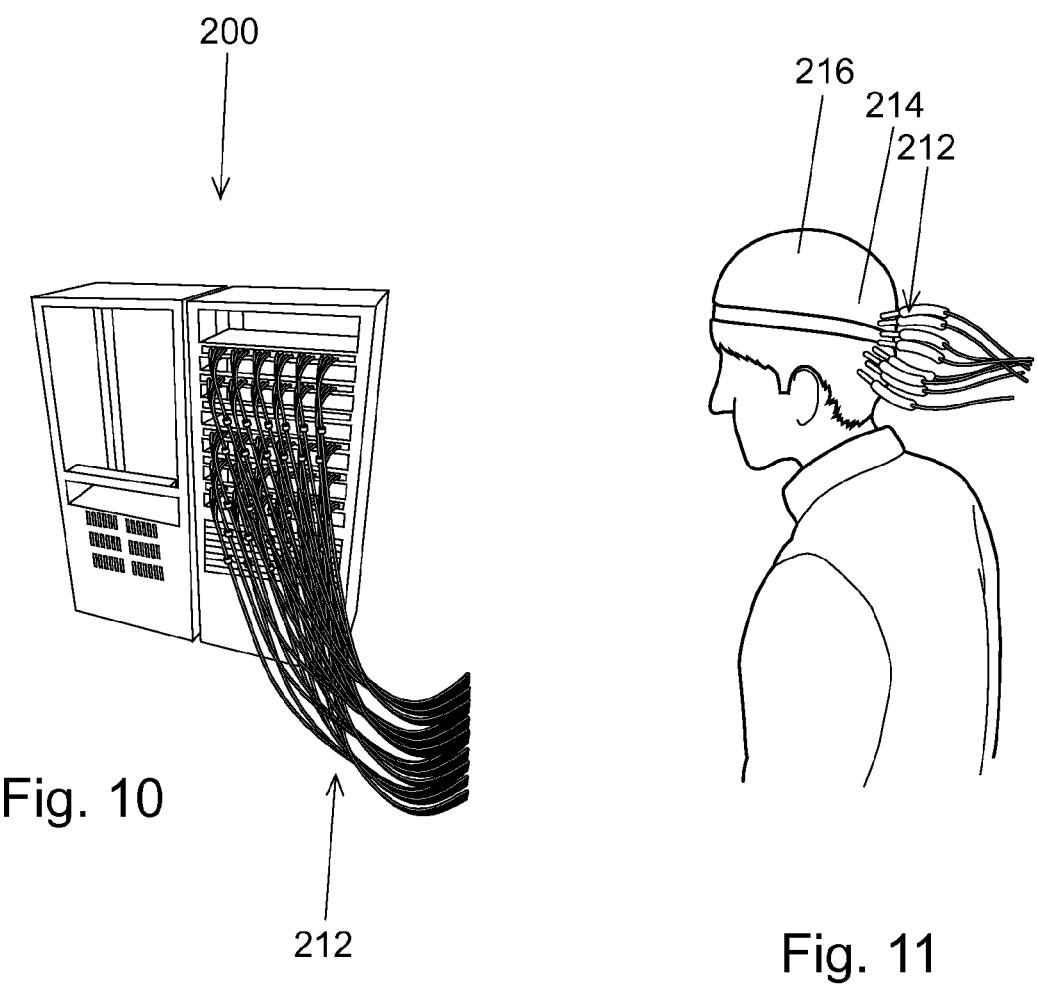
FIG. 10 is a perspective view of the main structure of the diffuse optical tomography system of the present invention.
FIG. 11 is a perspective view of human user and sources and detectors of the diffuse optical tomography system of the present invention.

In FIG. 11, there is a user 216 with the various electrical connectors to both the sources and detectors indicated again by numeral 212. The sources and detectors are indicated generally by numeral 214. The system avoids the limitations of dynamic gain switching and instead utilizes high instantaneous dynamic ranges greater than $10^7$ and crosstalk rejection less than $10^{-6}$.

The present invention utilizes very flexible software and/or firmware (which is computer software embedded in hardware) configurable in coding and decoding strategies with both discrete source and detector channel circuitry for both flexibility and improved channel separation. The present invention records first ($1^{st}$), second ($2^{nd}$) and third ($3^{rd}$) fourth ($4^{th}$) and fifth ($5^{th}$) nearest neighbor optode pair data instantaneously without gain switching. If the encoding of the sources is changed, no change will be necessary on the detector side since all detectors are recording with the same sensitivity at all times. The gain of flexibility and speed is a direct result of the fact that full dynamic range and crosstalk rejection is maintained at the full encoding rate.

Figure 12:
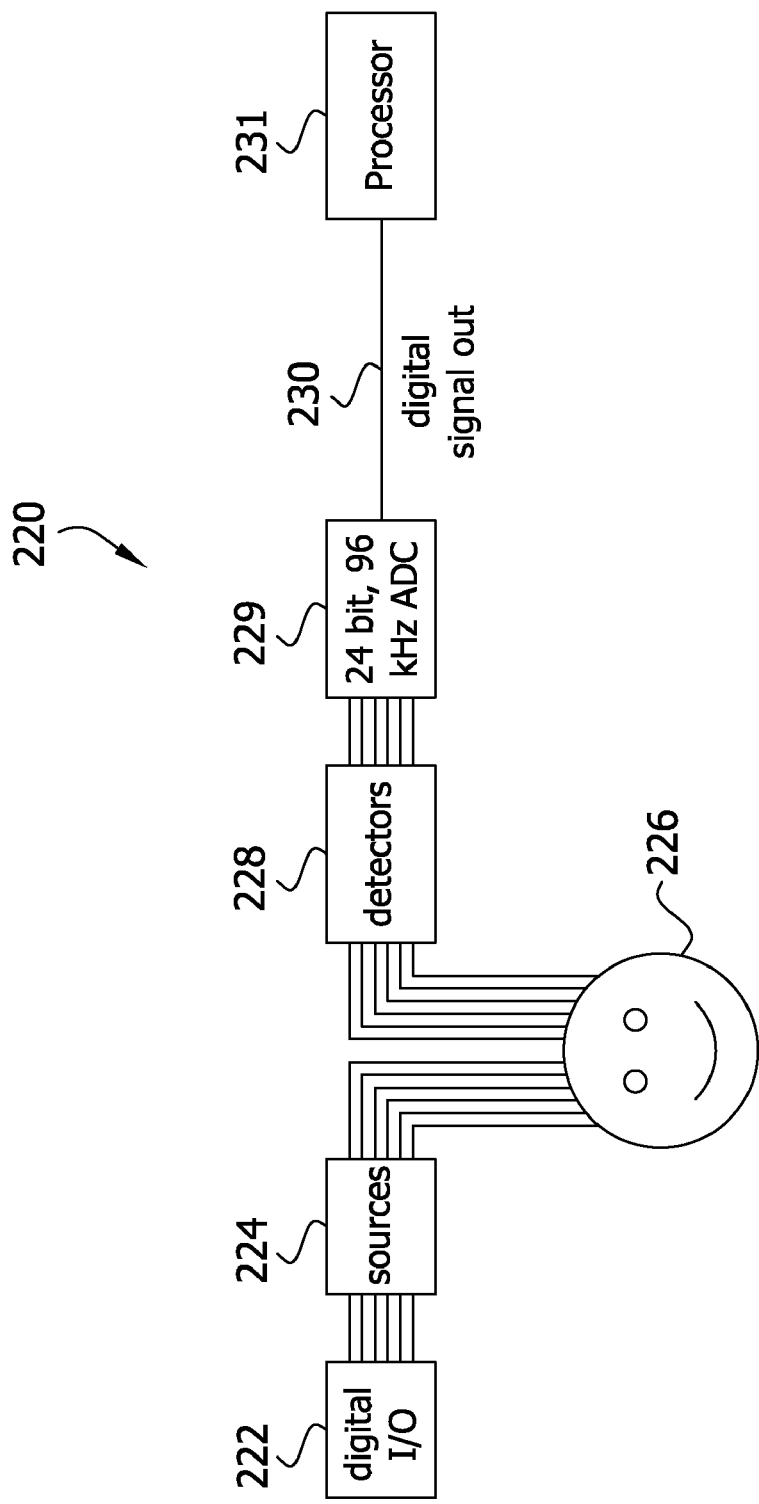
FIG. 12 is a flowchart of the diffuse optical tomography system of the present invention.

Referring now to FIG. 12, the system of the present invention is generally indicated by numeral 220. This system 220 includes digital input and output and provides power to the sources 224. The sources 224 preferably, but not necessarily, include light emitting diodes ("LEDs"). Optimally, but not necessarily, these LEDs 224 are shaved down and polished so that the face of each LED 224 is within a range from about 0.1 to about 2 millimeters of the light producing element and more preferably in a range from about 0.2 to about 0.5 millimeters of the light producing element and most preferably in a range from about 0.1 to about 0.3 millimeters of light producing element.

These sources 224 utilize fiber optics to transfer the light to the head through a molded optode grid design. Preferably the body of the molded optode grid design is a customized thermoplastic sheet that fits on the back of the head and is held with VELCRO® straps across the forehead. The user is indicated by numeral 226.

The source light is received by the main photo-diode detectors 228, e.g., avalanche photo diode detectors ("APDs"). Avalanche diodes 228 provide a dynamic range greater than $10^7$. These signals are then received by an analog digital converter 228. An illustrative, but nonlimiting, example would include a 24 bit, 96 KHz analog-to-digital converter ("ADC"). The analog-to-digital converter is indicated by numeral 229 with the output digital signal indicated by numeral 230. The output digital signals are then electrically connected to a processor 231. The processor 231 can be a digital signal processor, a personal computer, or a controller, however, any of a wide variety of electronic computers or electronic controllers will suffice.

Figure 13:
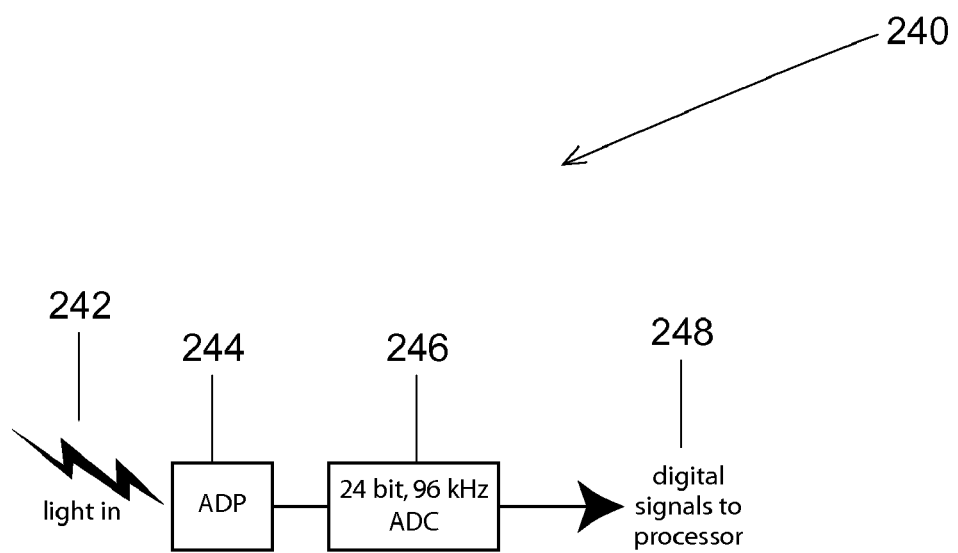
FIG. 13 is a flowchart of the detection system of the diffuse optical tomography system of the present invention.

The detector system associated with the present invention is generally indicated by numeral 240 in FIG. 13. The received source light is indicated by numeral 242, which is received by channel dedicated receivers, e.g., avalanche photo diode ("APD"), indicated by numeral 244 and then received by an analog-to-digital converter ("ADC") indicated by numeral 246 which provides digital signals to a processor 248, e.g., computer. An illustrative, but nonlimiting, example of an ADC includes a 24 bit 96 KHz ADC, as shown in FIG. 13, which is generally indicated by numeral 246.

Figure 14A:
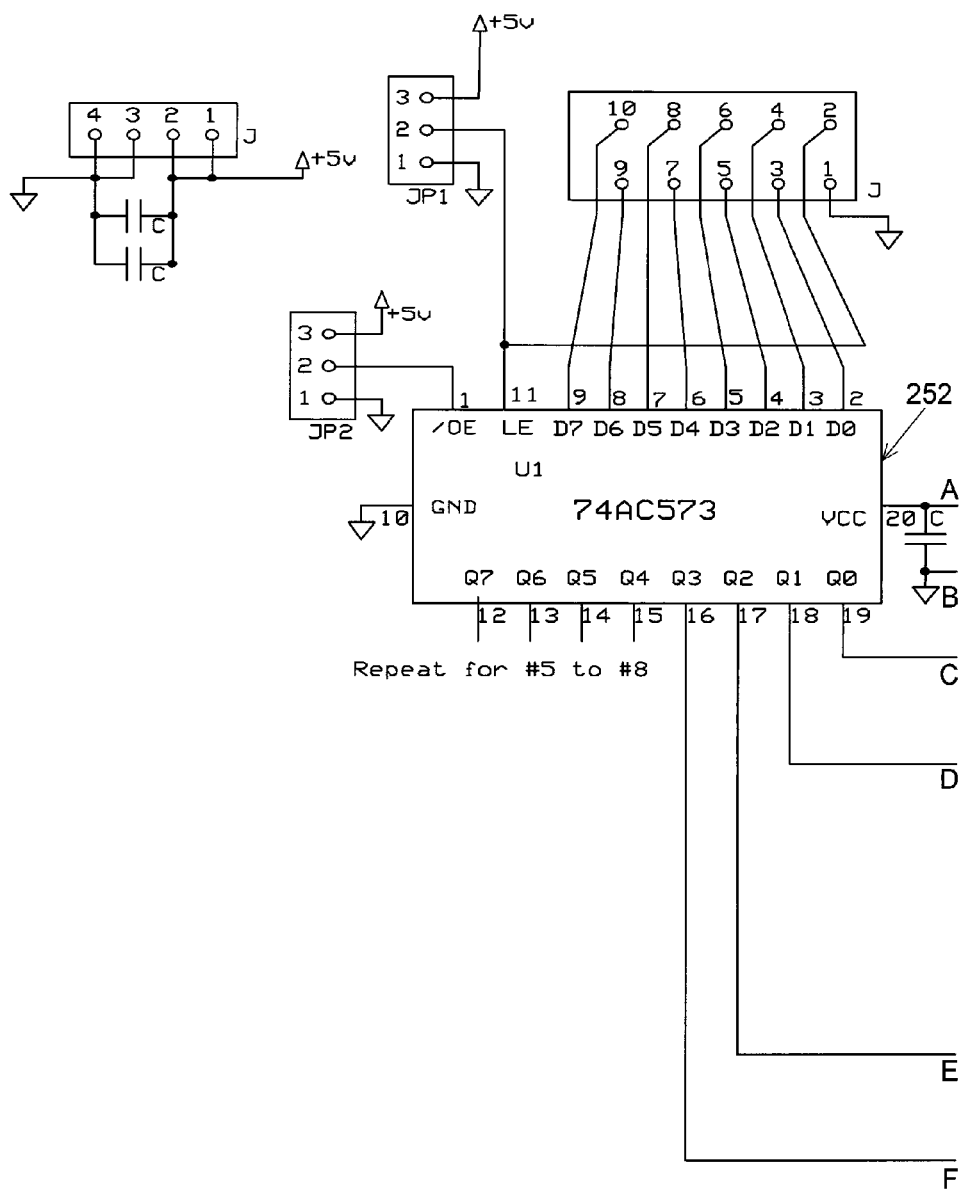
FIG. 14 is an illustrative, but nonlimiting, electrical schematic of control circuitry associated with the light emitting diodes of the diffuse optical tomography system of the present invention.
Figure 14B:
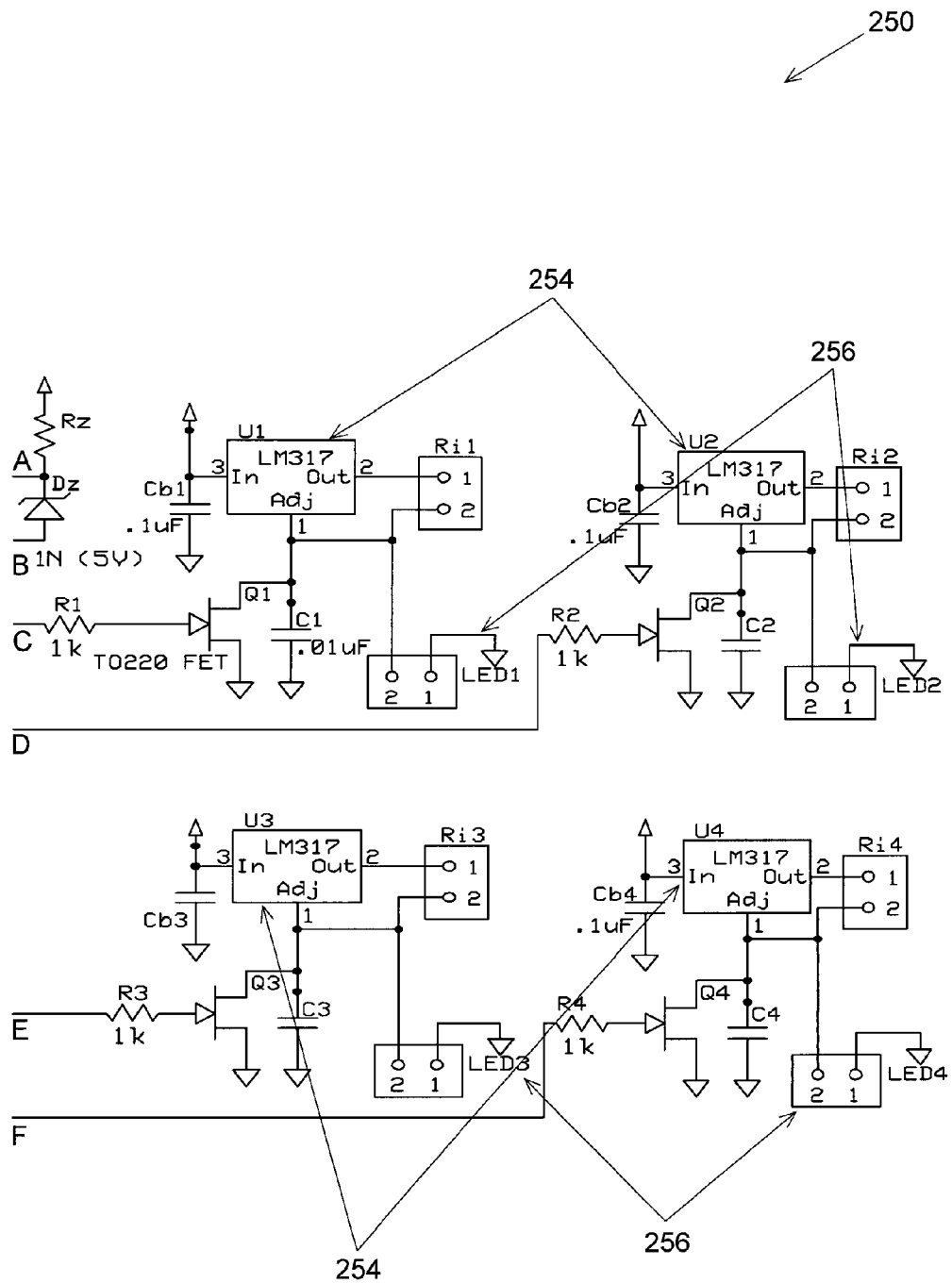

As shown in FIG. 14, an illustrative, but nonlimiting, example of the light emitting driver circuit is generally indicated by numeral 250 and includes an octal latch, e.g., 74AC573, generally indicated by numeral 252 which is connected to a series of voltage regulators 254, e.g., LM317. Each voltage regulator 254 is connected to a light emitting diode 256. This illustrative schematic of the custom circuitry is for eight (8) light emitting diode sources controlled from each circuit board.

Figure 15A:
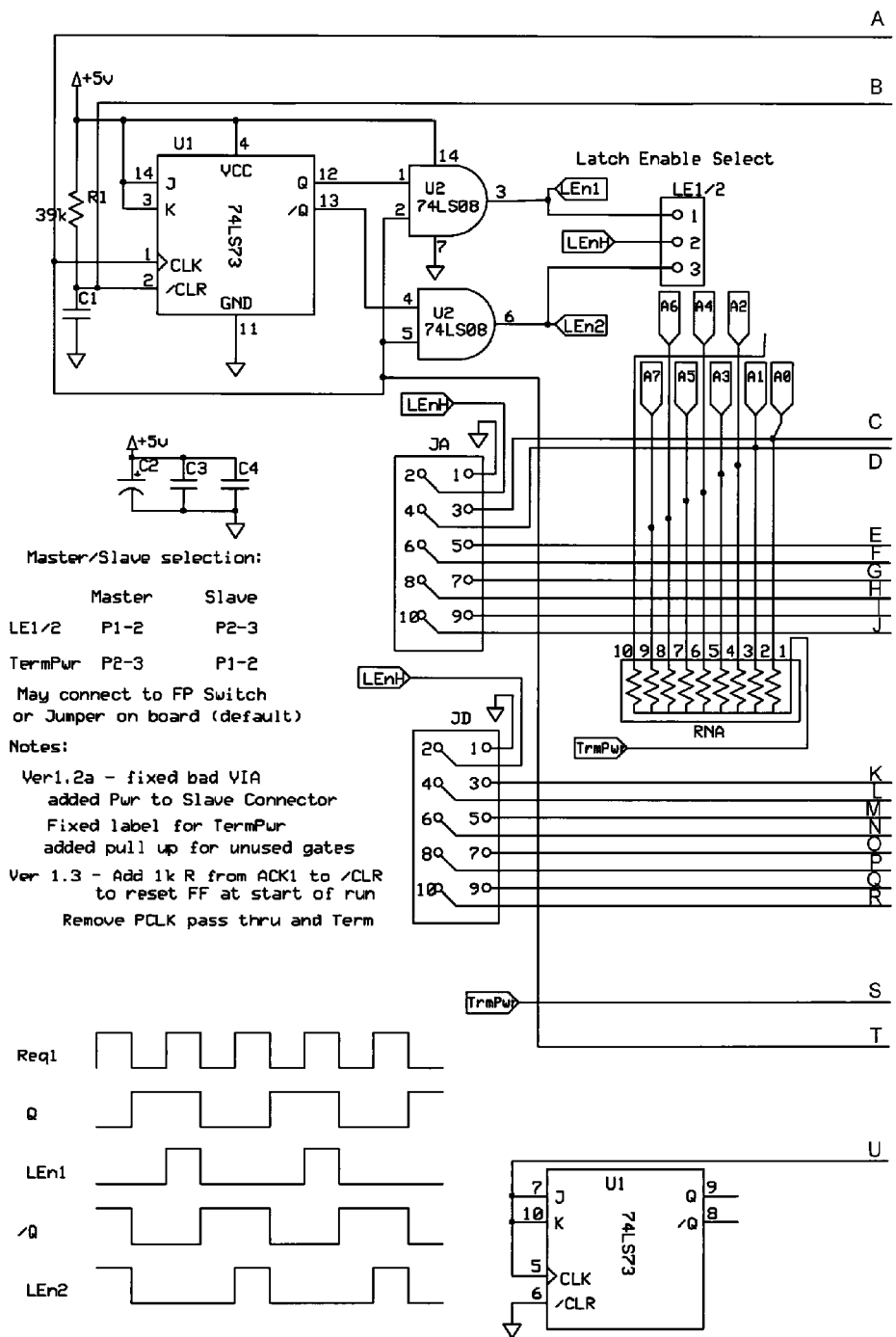
FIG. 15 is an illustrative, but nonlimiting, electrical schematic of signal breakout circuitry associated with the light emitting diodes of the diffuse optical tomography of the present invention.
Figure 15B:
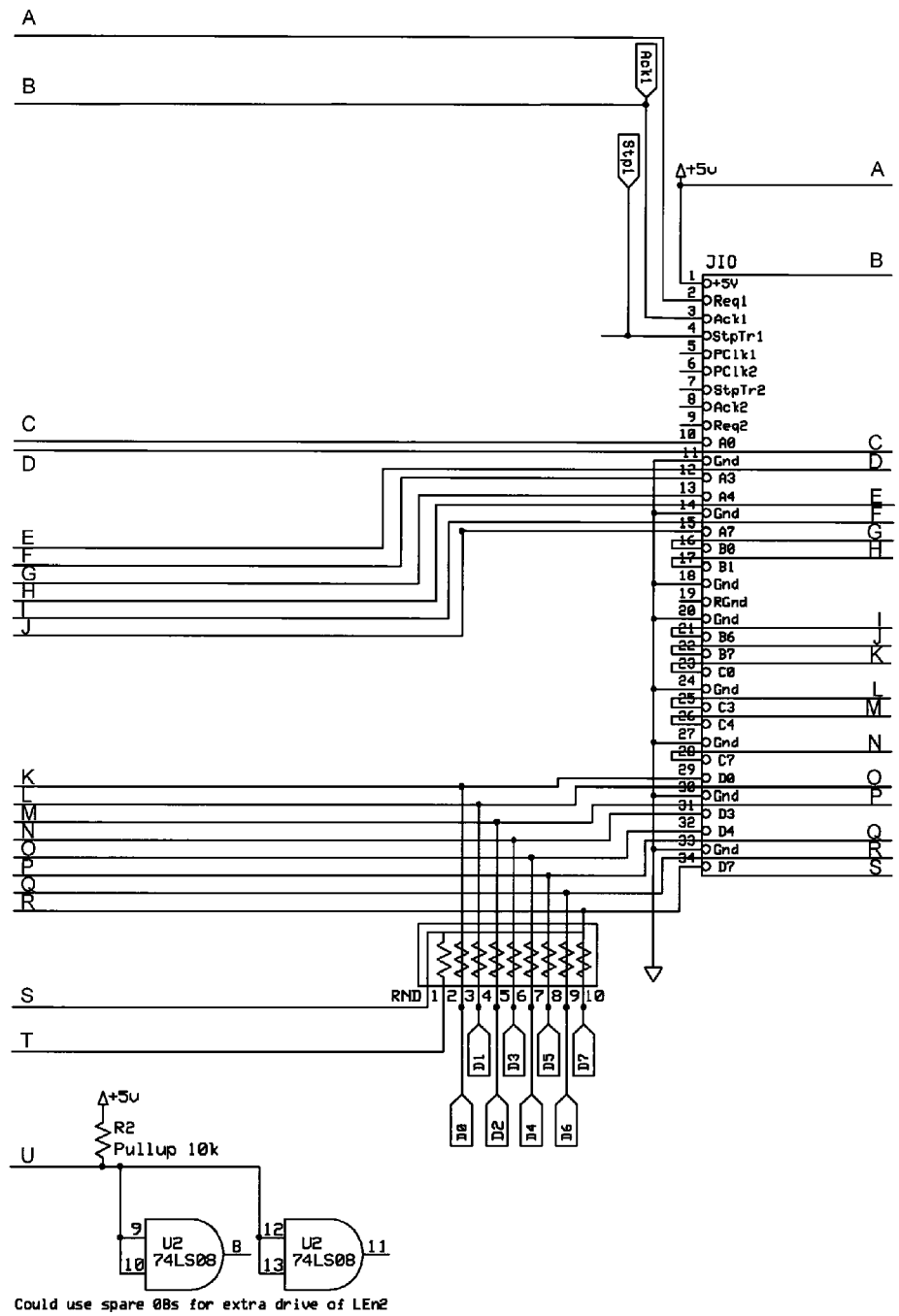
Figure 15C:
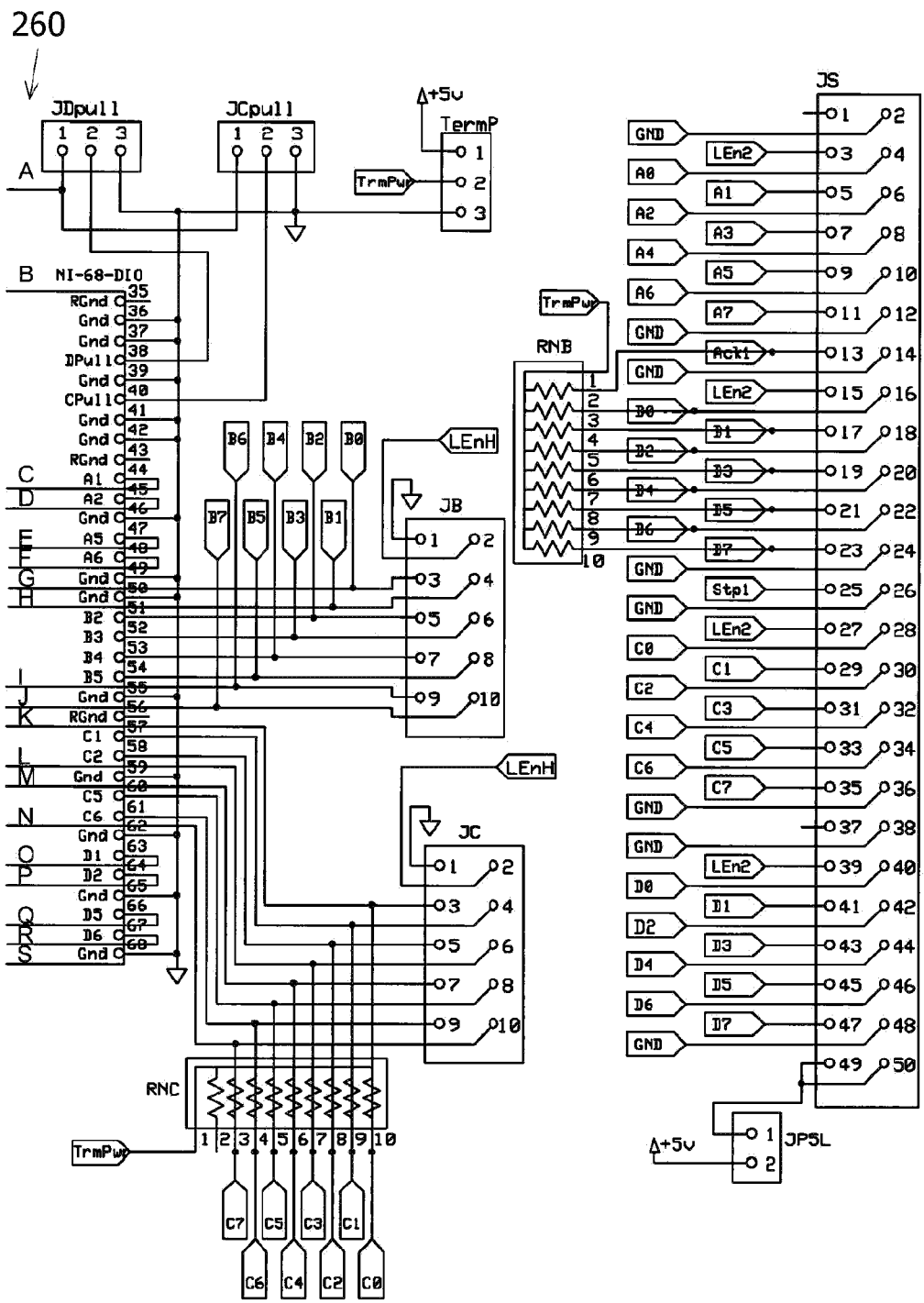

An illustrative, but nonlimiting, example of a signal breakout circuit for the source is generally indicated by numeral 260 in FIG. 15. The schematic divides the digital input/output lines and sends the signals to the appropriate source, e.g., light emitting diode.

Therefore, the present invention achieves high performance at high speed with a high dynamic range, low crosstalk with a system of discrete isolated power supplies. Each light source has a dedicated high-bandwidth control line, e.g., 20 megahertz (digital input/output line that can be individually programmed). The source multiplexing takes place entirely within the digital domain. Each light source, e.g., light emitting diode, has individual, isolated power supply to reduce crosstalk. Light emitting diodes as well as laser diodes have a threshold voltage below which they do not produce any light. When utilized in conjunction with individual digital control lines, the threshold voltage will squelch crosstalk. The small signal will not produce a light emitting diode output. Therefore, as a result of the above listed features, there is no measurable optical (light) crosstalk between source channels. Also, although the source control is digital, the high bandwidth at the control lines allows for variable intensity control of the sources through a high rate, variable duty pulsing. Also, the present invention allows for use of quad furcated optical fibers with two or more colors of light multiplexed through a single source location.

The present invention achieves high performance at high speed with a high dynamic range and low crosstalk with a system of discrete, isolated avalanche photo diodes ("APDs"). Each detector channel has a dedicated APD so no gain switching is necessary. There are preferably isolated power sources for each APD for signal isolation and to reduce crosstalk. High-end commercial analog-to-digital converters ("ADCs"), e.g., 24 bit ADC, are utilized to digitize the signal output. A channel dedicated line eliminates gain switching. The units have very little noise and inter-channel crosstalk and all the data can be stored directly to a hard disk in real time with a sampling rate, e.g., 96 KHz. The separation of signals, otherwise known as decoding frequency encoding, is preferably carried out with software which allows maximum flexibility to determine the number of encoding frequencies.

These instrumentation advances facilitate the use of a number of algorithms. Firsts the instrument supports DOT synthesis of the data into three dimensional images. These images can be created using any of the reported DOT approaches available in the literature. This includes, but is not limited to, J. Culver, A. Siegel, J. Stott, and D. Boas, *Volumetric Diffuse Optical Tomography Of Brain Activity*, Nov. 1, 2003, Vol. 28, No. 21, Pages 2061-2063, OPTICS LETTERS and J. Culver, T. Durduran, D. Furuya, C. Cheung, J. Greenberg, and A. G. Yodh, *Diffuse Optical Tomography of Cerebral Blood Flow, Oxygenation, and Metabolism in Rat During Focal Ischemia*, Journal of Cerebral Blood Flow & Metabolism, 23:911-924, The International Society for Cerebral Blood Flow and Metabolism, Published by Lippincott Williams & Wilkins, Inc., Baltimore.

A nonlimiting but illustrative example includes reconstructing human brain activation using the following algorithms. A wide variety of models may be utilized. This includes, but is not limited to, a homogeneous model, a layered model, a sphere model, a hemisphere model, a cylindrically-shaped model, or an anatomically derived model. As an illustrative, nonlimiting example, a two-layer, hemispheric head model (radius is equal to 80 millimeters) was used for finite-element, forward light modeling, e.g., Near Infrared Frequency domain Absorption and Scatter Tomography ("NIRFAST"), to obtain a sensitivity matrix for the optode array. An illustrative, but nonlimiting, example of NIRFAST is disclosed in Dehghani H, Pogue B W, Poplack S P, Paulsen K D, *Multiwavelength Three-Dimensional Near-Infrared Tomography of the Breast: Initial Simulation, Phantom, and Clinical Results*, Applied Optics 2003; 42:135-145. The model for a human head has a 15 millimeter scalp/skull layer surrounding the brain with a radius equal to 65 millimeters. The optical properties of absorption coefficient $\mu_a$ and the reduced scattering coefficient $\mu'_s$ for the two layers can be obtained from technical literature. For example, for the outer scalp/skull layer: $\mu_a$=0.15 cm$^{-1}$, $\mu'_s$=8.4 cm$^{-1}$ at 750 nanometers and $\mu_a$=0.17 cm$^{-1}$, $\mu'_s$=7.4 cm$^{-1}$ at 850 nanometers. In a similar manner for the brain: $\mu_a$=0.19 cm$^{-1}$, $\mu'_s$=12 cm$^{-1}$ at 750 nanometers and $\mu_a$=0.19 cm$^{-1}$, $\mu'_s$=1 cm$^{-1}$ at 850 nanometers.

The original tetrahedral finite-element forward model was transformed into a voxel space (2 mm voxels) through a weighted spatial average to create the sensitivity matrix for the instrument. The linear Rytov approximation is expressed as y=Ax, using a discrete node representation for images of absorption perturbations, x, where y is a vector of differential light measurements and A is the sensitivity matrix constructed with an adjoint formulation.

The finite-element forward model was directly inverted for image reconstruction following previously established procedure known in the technical literature. The inverse problem will minimize the objective function: $\min\{\|C^{-1}(y_{meas}-Ax)\|_2^2 + \alpha\|Lx\|_2^2\}$ A diagonal covariance matrix C is utilized that incorporates a shot noise model of measurement noise. The penalty term for image variance is $\alpha\|Lx\|_2^2$ incorporated spatially variant regularization where the diagonal of L=(diag $(A^T A)+\beta)^{1/2}$. A solution, i.e., $x=A_{\beta,\alpha}{}^{\#} y_{meas}$, was obtained using a Moore-Penrose generalized inverse with, $A_{\beta,\alpha}{}^{\#}= L^{-1}\tilde{A}^T(\tilde{A}^T\tilde{A}+\alpha I)^{-1} y_{meas}$ where $\tilde{A}=\tilde{A}L^{-1}$. The optimal values of $\alpha$=0.0005 and $\beta$=0.1 were found to provide even imaging across the field of view as judged by an evaluating point, line and half-space objects using a resolution matrix analysis and contrast to noise assessments.

Hemoglobin concentrations ("C") were obtained from the absorption coefficients using spectral decomposition, i.e., $\Delta C=E^{-1}\Delta\mu$, where $\Delta C=\{\Delta[Hb_R], \Delta[HbO_2]\}$ is a vector of concentrations, E is a matrix containing the extinction coefficients of $Hb_R$ and $HbO_2$ at the two wavelengths, and $\Delta\mu_a=\{\Delta\mu_a{}^{750\,nm}, \Delta\mu_a{}^{850\,nm}\}$ is a vector containing the differential absorption coefficients.

Another aspect of the present invention is that the dense grid allows noise reduction methods to be utilized. One class of noise reduction algorithms removes noise from the data prior to reconstruction of the images. Physiological fluctuations in the scalp and skull are a confound in all non-invasive optical imaging. However, by taking advantage of the dense grid and high-dynamic range of the present invention, a method that makes use of the scalp bias of the first (1$^{st}$) nearest neighbor measurements to remove the background and superficial signals is available. In the unfiltered time-course of a single second (2$^{nd}$) nearest neighbor standard deviation ("SD") pair for all fifteen blocks, the visual response signal is obscured which is indicated on the graph that is generally indicated by numeral 300 and shown in FIG. 16 as indicated by numeral 302. The background physiological signals are removed from the raw signal trace 302 to provide signals in which activation responses can be clearly identified 304 as a method to improve activation to background ratios.

A computationally efficient linear regression approach can be used to reduce background signals. Nonlimiting examples of a computationally efficient linear regression approach can include fMRI data and simulated NIRS data. An illustrative, but nonlimiting, example of utilizing fMRI data is disclosed in Fox M D, Snyder A Z, Vincent J L, Corbetta M, Van Essen D C, Raichle M E, *The Human Brain is Intrinsically Organized into Dynamic, Anticorrelated Functional Networks*, Proceedings of the National Academy of Sciences of the United States of America 2005; 102:9673-9678. An illustrative, but nonlimiting, example of utilizing simulated NIRS data is disclosed in Saager R B, Berger A J, *Direct Characterization and Removal of Interfering Absorption Trends in Two-Layer Turbid Media*, Journal of the Optical Society of America a-Optics Image Science and Vision 2005; 22:1874-1882.

Starting with the log-ratio optode pair measurements (y'$_i$), the mean of the first (1$^{st}$) nearest neighbor measurements (y'$_{nn}$) is removed from the all y'$_i$ through linear regression using $$y_i = y'_i - \frac{\langle y_{nn}, y'_i \rangle}{\langle y_{nn}, y_{nn} \rangle} y'_i.$$

The resulting time traces y$_i$ are then used for reconstruction.

Figure 16:
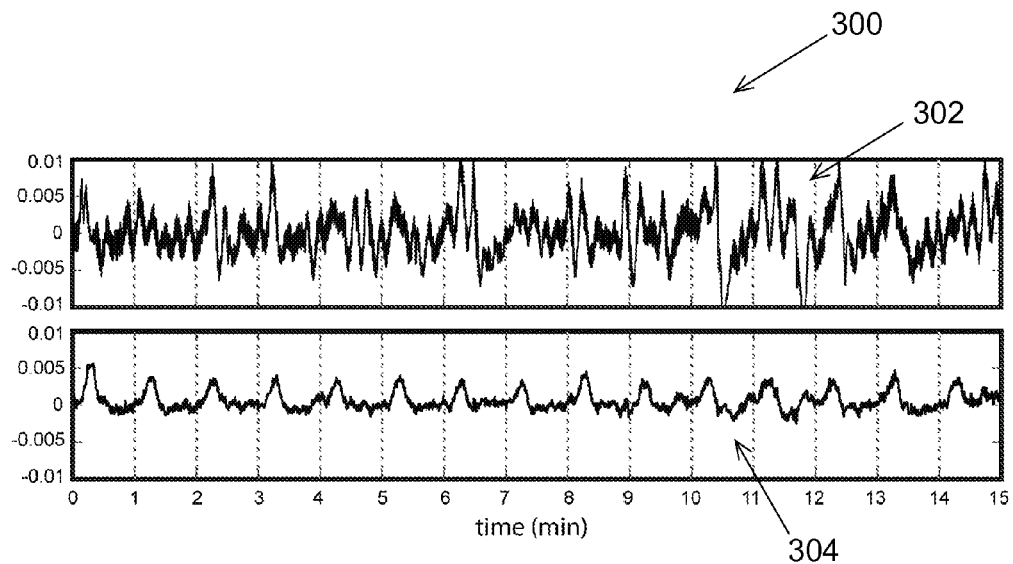
FIG. 16 is a graphical representation of improved activation to background ratios with covariance analysis to remove background physiological signals from the raw signal to provide signals where the activation response is clearly identified.

The application of a covariance analysis removes a common-mode signal, and the individual visual responses can be seen in each of the fifteen blocks 304 as shown in FIG. 16. The activation contrast-to-noise ratio ("CNR") is increased by a factor of five. The high CNR allows the creation of tomographic image reconstructions of individual stimulus blocks (not shown). In contrast to blind source separation procedures that treat all measurement channels equivalently, this procedure incorporates knowledge of where a signal is present, e.g., brain and second (2$^{nd}$) nearest neighbor pairs, and where a signal is absent, e.g., scalp and first (1$^{st}$) nearest neighbor pairs. This approach has not been previously used with imaging systems and requires a dense grid system to provide the combination of first (1$^{st}$) nearest neighbor and second (2$^{nd}$) nearest neighbor measurements.

Alternatively, high definition data ("HD-Data") also supports use of blind methods of signal extractions. For example, independent component analysis can be used to separate out activation signals from noise. Illustrative, but nonlimiting, examples, are described in Hyvarinen A., *Fast and Robust Fixed-Point Algorithms for Independent Component Analysis*, IEEE Transactions on Neural Networks, 1999; 10:626-634 and Hyvarinen A, Oja E, *Independent Component Analysis Algorithms And Applications*, Neural Networks 2000; 13:411-430.

Independent component analysis ("ICA") is a computational method for separating a multivariate signal into additive subcomponents supposing the mutual statistical independence of the non-Gaussian source signals. It is a special case of blind source separation defined by x=As where each mixture signal (row of x) is a weighted, linear sum of the source signals (rows of s) and the contribution of each source signal to each mixture signal is unknown. Given a set of M observed mixture signals where each signal consists of N time points, ICA estimates K (K$\leq$M) statistically independent source components and estimates the mixing matrix A using contrast functions such as "tanh" or "skew" to rank statistical independence. This approach has been applied to many biological signals including EEG and fMRI data. Signals of interest can be extracted as well as noise signals. An illustrative, but nonlimiting, example of applying this approach to EEG data signals is disclosed in: Onton J, Westerfield M, Townsend J, Makeig S, *Imaging Human EEG Dynamics Using Indepen-* dent Component Analysis, Neuroscience and Biobehavioral Reviews 2006; 30:808-822. An illustrative, but nonlimiting, example of applying this approach to fMRI data signals is disclosed in Mantini D, Perrucci M G, Cugini S, Ferretti A, Romani G L, Del Gratta C., *Complete Artifact Removal For EEG Recorded During Continuous Fmri Using Independent Component Analysis*, Neuroimage 2007; 34:598-607.

As a nonlimiting, but illustrative example, we have applied ICA to functional activation data for mapping the visual response to a stationary flickering checker board quadrant. Starting with a set of 212 standard deviation ("SD") pair time courses (first ($1^{st}$) and second ($2^{nd}$) nearest neighbors, 100 seconds), we obtained K=12 components. Of the twelve independent components, two appeared (by visual inspection) to be "noise" due to heart and respiration signals. The ten that were non-noise components were used to reconstruct the set of 212 signals free of the heart component.

Figure 17:
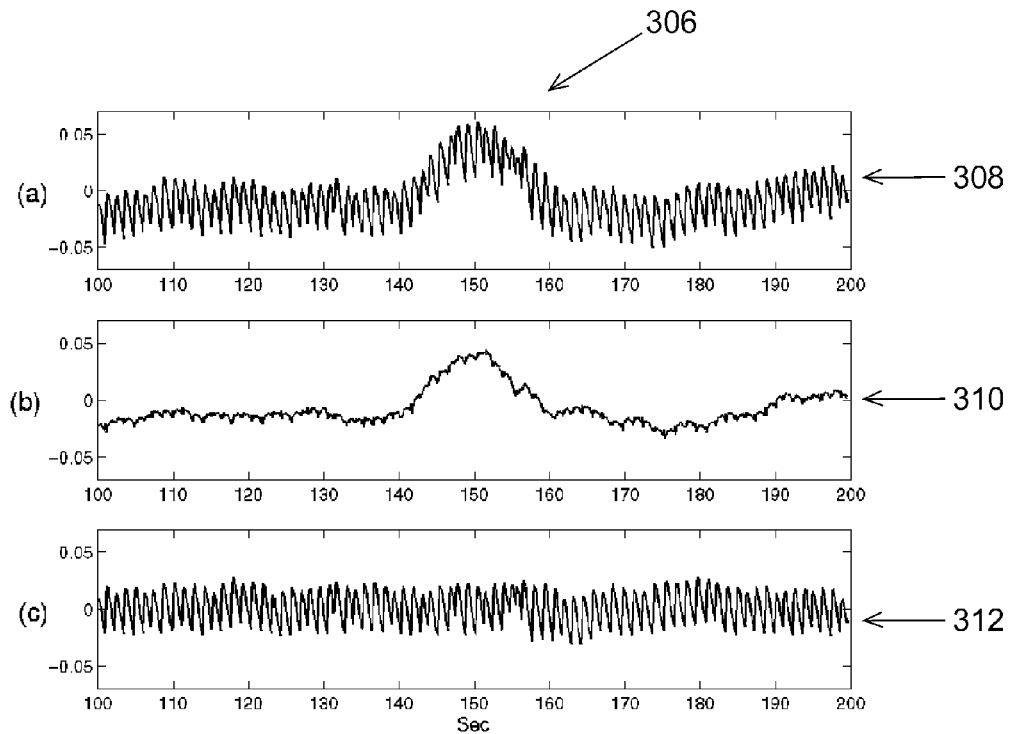
FIG. 17 is a graphical representation of improved activation to background ratios with covariance analysis with an originally observed standard deviation pair signal with a visual stimulus, the activation signal in reconstructed standard deviation pair from a predetermined number, e.g., 10, of the independent component analysis components, and noise in the signal by mapping only a predetermined number, e.g., two, of the noise components back into standard deviation pair representation.

Referring now to FIG. 17, displays plots for an individual SD-pair as generally indicated by numeral 306. This includes the original observed signal 308 with a visual stimulus occurring between times 140-to-150 seconds, the cleaned activation signal in reconstructed SD-pair data from ten ICA non-noise (components) signals 310 and the noise in the signal generated from the two noise components 312 by mapping only the two noise components back into standard deviation ("SD") pair representation. The analysis clearly separates the heart signal or "noise" from the activation signal. This approach has great potential for removing other less predictable spurious noise sources such as movement artifacts and systemic blood pressure oscillations.

Alternative configurations of the source modules include use of any other solid state light emitters, including but not limited to laser diodes, super luminescent emitting diodes, and solid state lasers, and other laser sources. Modulation can be accomplished either by modulating light generation, or by modulating light transmission after generation. Alternate detectors include photodiodes, and photomultiplier tubes.

Alternate modes of detection include fluorescence and the use of fluorescing agents. For instance, using the preferred device described above, filters could be placed in front of each detector to reject the excitation light and permit detection of fluorescence emission light. Using a bolus injection of a fluorescent agent, (e.g. indocyanine green dye, which is FDA approved or newly developed targeted agents) one could monitor the dynamic distribution of the fluorescing agent in the brain.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "have," "having," "includes" and "including" and similar terms as used in the foregoing specification are used in the sense of "optional" or "may include" and not as "required." Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims that follow.

The invention claimed is:

1. An imaging system for diffuse optical tomography comprising:

a plurality of light sources, each light source being connected to a separate, isolated digitally controlled power source and being isolated from each other light source;

a plurality of light conduits connected to the plurality of light sources;

an optode grid attachable to a portion of a human subject, wherein the optode grid is connected to the plurality of light conduits;

a plurality of detector channels connected to the optode grid for receiving light from the plurality of light sources after interacting with the human subject;

a plurality of light detectors, each light detector being coupled to only one of the detector channels for instantaneously detecting light received by its coupled channel, each light detector having a separate, isolated power source; and a plurality of analog to digital converters (ADCs), each ADC connected to only one light detector and converting signals from its connected light detector into a separate digital signals for use in imaging.

2. The imaging system for diffuse optical tomography of claim 1, wherein each digitally controlled power source modulates at a high bandwidth up to 20 megahertz.

3. The imaging system for diffuse optical tomography of claim 1, wherein the plurality of light sources includes a plurality of light emitting diodes.

4. The imaging system for diffuse optical tomography of claim 1, wherein the plurality of light sources is selected from the group consisting of laser diodes, super luminescent emitting diodes, solid state lasers, or other laser sources.

5. The imaging system for diffuse optical tomography of claim 1, wherein the plurality of light conduits includes a plurality of fiber optic cables.

6. The imaging system for diffuse optical tomography of claim 5, wherein at least one of the plurality of fiber optic cables is multi-furcated to receive multiplex light from a single source.

7. The imaging system for diffuse optical tomography of claim 1, wherein each digital input power source is utilized in conjunction with a threshold voltage to minimize crosstalk.

8. The imaging system for diffuse optical tomography of claim 1, wherein the light detectors includes avalanche photo diodes.

9. The imaging system for diffuse optical tomography of claim 1, wherein the light detectors are selected from the group consisting of photodiodes or photomultiplier tubes.

10. The imaging system for diffuse optical tomography of claim 1, wherein the optode grid is a molded component that is attachable to a portion of a human subject with straps.

11. The imaging system for diffuse optical tomography of claim 1, further comprising a processor that generates a model selected from the group consisting of a homogeneous model, a layered model, a sphere model, a hemisphere model, a cylindrically-shaped model, or an anatomically derived model with finite element analysis from the plurality of digital signals.

12. The imaging system for diffuse optical tomography of claim 11, wherein finite element analysis includes finite element, forward light modeling.

13. The imaging system for diffuse optical tomography of claim 1, further includes a processor that utilizes at least one noise reduction algorithm on the plurality of digital signals.

14. The imaging system for diffuse optical tomography of claim 13, wherein said at least one noise reduction algorithm includes linear regression covariance analysis with an increase in contrast-to-noise ratio.

15. The imaging system for diffuse optical tomography of claim 13, wherein the at least one noise reduction algorithms includes independent component analysis.

16. An imaging system for diffuse optical tomography comprising:
- a plurality of light emitting diodes, each light emitting diode being connected to a separate, isolated digital input power source and being isolated from each other light emitting diode;
- a plurality of fiber optic cables connected in a one-to-one relationship to the plurality of light emitting diodes;
- an optode grid attachable to a portion of a human subject, wherein the optode grid is connected to the plurality of fiber optic cables;
- a plurality of detector channels connected to the optode grid for receiving light from the plurality of light emitting diodes after interacting with the human subject;
- a plurality of avalanche photo diodes, each avalanche photo diode being coupled to only one of the detector channels for detecting light received by its coupled channel, each avalanche photo diode having a separate isolated power source; and
- a plurality of analog to digital converters (ADCs), each ADC connected to only one avalanche photo diode and converting signals from its connected avalanche photo diodes into a separate digital signals for imaging.

17. A method for utilizing an imaging system for diffuse optical tomography comprising:
- attaching an optode grid to a portion of a human subject, wherein the optode grid design is connected to the plurality of light conduits that are connected to a plurality of light sources, wherein each light source is electrically connected to a separate, isolated digital input power source, and wherein each light source has a separate digital control input for individual programming;
- utilizing a plurality of light detectors that are connected to the optode grid via a plurality of detector channels for instantaneously detecting light received at the detector channels, said received light provided by the plurality of light sources after interacting with the human subject, wherein each light detector is coupled to only one of the detector channels, and wherein each light detector has a separate, isolated power source; and
- converting a plurality of individual signals from the plurality of light detectors into a plurality of digital signals for imaging with a plurality of analog to digital converters (ADCs), wherein each ADC connects to only one light detector, and wherein each ADC converts signals only from its connected light detector.

18. The method for utilizing an imaging system for diffuse optical tomography according to claim 17, further includes providing signals at a high speed in a high dynamic range to each digital input power source.

19. The method for utilizing an imaging system for diffuse optical tomography according to claim 17, wherein the plurality of light sources is selected from the group consisting of light emitting diodes, laser diodes, super luminescent emitting
diodes, solid state lasers, or other laser sources, and the plurality of discrete, isolated, light detectors is selected from the group consisting of avalanche photo diodes, photodiodes or photomultiplier tubes.

20. The method for utilizing an imaging system for diffuse optical tomography according to claim 17, further includes generating a model selected from the group consisting of a homogeneous model, a layered model, a sphere model, a hemisphere model, a cylindrically-shaped model, or an anatomically derived model with finite element analysis with a processor from the plurality of digital signals.

21. The method for utilizing an imaging system for diffuse optical tomography according to claim 17, further includes utilizing at least one noise reduction algorithm with a processor on the plurality of digital signals, wherein the at least one noise reduction algorithm is selected from the group consisting of linear regression covariance analysis and independent component analysis.

22. The method for utilizing an imaging system for diffuse optical tomography according to claim 17, further includes utilizing filters positioned in front of the plurality of light detectors for detecting fluorescing agents in a human body.

23. The imaging system for diffuse optical tomography of claim 1, wherein the plurality of light sources are multiplexed in the digital domain.

24. The imaging system for diffuse optical tomography of claim 23, wherein an integrated intensity of the plurality of light sources is controlled by a variable duty cycle for extending the effective dynamic range of the detector.

* * * * *

UNITED STATES PATENT AND TRADEMARK OFFICE
CERTIFICATE OF CORRECTION

PATENT NO. : 7,983,740 B2
APPLICATION NO. : 11/962513
DATED : July 19, 2011
INVENTOR(S) : Culver et al.

Page 1 of 1

It is certified that error appears in the above-identified patent and that said Letters Patent is hereby corrected as shown below:

Column 12, Claim 1, Line 21: "signals" should read --signal--.

Column 13, Claim 16, Line 26: "diodes" should read --diode--.

Signed and Sealed this
Twenty-sixth Day of June, 2012

David J. Kappos
*Director of the United States Patent and Trademark Office*